US008928872B2

(12) United States Patent
Muller et al.

(10) Patent No.: US 8,928,872 B2
(45) Date of Patent: Jan. 6, 2015

(54) TEMPERATURE MODULATED REFRACTIVE INDEX MEASUREMENT

(75) Inventors: Ulrich Muller, Konz (DE); Jan Kristian Kruger, Saarbrucken (DE)

(73) Assignee: Anton Paar Optotec GmbH (DE)

( * ) Notice: Subject to any disclaimer, the term of this patent is extended or adjusted under 35 U.S.C. 154(b) by 44 days.

(21) Appl. No.: 13/818,102

(22) PCT Filed: Aug. 2, 2011

(86) PCT No.: PCT/EP2011/063311
§ 371 (c)(1),
(2), (4) Date: Feb. 21, 2013

(87) PCT Pub. No.: WO2012/025346
PCT Pub. Date: Mar. 1, 2012

(65) Prior Publication Data
US 2013/0155395 A1 Jun. 20, 2013

(30) Foreign Application Priority Data
Aug. 23, 2010 (LU) .......................................... 91723

(51) Int. Cl.
*G01N 21/41* (2006.01)
*G01N 21/43* (2006.01)
*G01N 21/17* (2006.01)

(52) U.S. Cl.
CPC .............. *G01N 21/41* (2013.01); *G01N 21/43* (2013.01); *G01N 2021/1731* (2013.01); *G01N 2201/0691* (2013.01)
USPC ............................ 356/128; 356/136; 374/161

(58) Field of Classification Search
CPC ................ G01N 2021/414; G01N 2021/1731; G01N 21/41; G01N 2201/0691

USPC ........... 356/128–137, 445; 374/161, 141, 142
See application file for complete search history.

(56) References Cited

U.S. PATENT DOCUMENTS

| 3,090,222 | A | 5/1963 | Michijiro Akaboshi et al. |
| 6,169,838 | B1 * | 1/2001 | He et al. .................. 385/129 |

(Continued)

FOREIGN PATENT DOCUMENTS

| EP | 0598968 A1 | 6/1994 |
| WO | 9117425 | 11/1991 |

OTHER PUBLICATIONS

International Search Report from corresponding International Application No. PCT/EP2011/063311, mailed Oct. 27, 2011.

(Continued)

*Primary Examiner* — Hoa Pham
(74) *Attorney, Agent, or Firm* — Polster Lieder

(57) ABSTRACT

The present invention is directed to temperature modulated refractive index measurement. In accordance with the invention a method for determination of the complex temperature coefficient of the refractive index of a sample is provided, wherein the determination of the complex temperature coefficient of the refractive index of the sample is based on a refractive index measurement. Furthermore, the refractive index of the sample is measured over a period of time, wherein the temperature of the sample is modulated over said period of time and the complex temperature coefficient of the refractive index is calculated on the basis of the refractive index measurement over the period of time and the temperature modulation over the period of time. Additionally, a measurement system, in particular comprising a temperature control system and a processing system to carry out the above method, is disclosed.

15 Claims, 2 Drawing Sheets

(56) References Cited

U.S. PATENT DOCUMENTS

| | | |
|---|---|---|
| 6,970,256 B1 | 11/2005 | Jackson |
| 7,456,942 B1 | 11/2008 | Curley et al. |
| 2006/0078257 A1* | 4/2006 | Park et al. .................. 385/37 |
| 2012/0099690 A1* | 4/2012 | Sato et al. .................. 376/216 |

OTHER PUBLICATIONS

Kohanzadeh Y et al., "Measurement of Refractice Index Change With Temperature Using Thermal Self-Phase Modulation", Applied Optics, Optical Society of America, US, vol. 12, No. 7, Jul. 1, 1973, pp. 1584-1587.

\* cited by examiner

TEMPERATURE MODULATED REFRACTIVE INDEX MEASUREMENT

CROSS-REFERENCE TO RELATED APPLICATIONS

The present invention is the US national stage under 35 U.S.C. §371 of International Application No. PCT/EP2011/063311, which was filed on Aug. 2, 2011 and which claims the priority of application LU 91723 filed on Aug. 23, 2010 the content of which (text, drawings and claims) is incorporated here by reference in its entirety.

TECHNICAL FIELD

The present invention is directed to refractive index measurement and to the determination of the temperature coefficient of the refractive index.

BACKGROUND OF THE INVENTION

Multiple methods as well as respective devices for measuring the refractive index of samples are known in the state of the art. Especially refractometry is used for measurement of the refractive index. For instance an Abbe refractometer can be used to measure the refractive index of a sample. Such a refractometer comprises a prism adjoining a sample and a light source being arranged to generate a beam of light travelling through the prism to the sample whereas one part of the beam is diffracted and another part of the beam is reflected at the prism-sample interface. This behavior can be described by Fresnel's law. The reflected part of the beam may be detected by means of a light detector. Above a critical angle of incidence that depends on the refractive index of the sample, the light is totally reflected. At the critical angle, the intensity of the reflected light changes substantially resulting in an intensity profile recorded by a light detector allowing thus an evaluation of the sample's refractive index. This general principle is known to the person skilled in the art for a long time. Furthermore, other methods are known for measuring the refractive index, as for example by means of a goniometric refractometer or ellipsometry.

The knowledge of the refractive index of a sample may result in important information on the properties of a sample. For instance, refractive index measurement is frequently used for the determination of alcohol or sugar concentrations.

Another interesting property for characterization of samples may be the temperature coefficient of the refractive index.

Document WO 91/17425 discloses an apparatus for analyzing optical properties of transparent objects comprising a light source and an analyzer cell having a cavity formed therein for receiving a sample. A beam of light is generated by the light source guided through the analyzer cell and the sample. Preferably an optical fiber is used as heat source. Furthermore, this document mentions, although not in detail, a method of determining the temperature coefficient of the refractive index of a fluid, basically comprising the steps of providing a cell with a fluid, creating a known (spatial) temperature gradient in the fluid between known points in a given plain, analyzing the refractive index profile of the fluid in said plane, and determining the temperature gradient coefficient of the refractive index of the fluid from the analyzed refractive index profile and known temperature gradient. Unfortunately, this method can only be used for liquid samples. Furthermore, the method is unsuitable for samples underlying a chemical reaction which necessitates a constant temperature extending over the whole sample. Especially in the case of chemical reactions it is often undesirable to have different temperature across the sample because this might strongly influence the complete reaction and/or might induce convective flow.

U.S. Pat. No. 6,970,256 B1 discloses another apparatus for measuring the thickness and refractive index of a sample. The apparatus comprises a prism mounted in a prism support, a sample in contact with one side of the prism and thermal elements for heating the sample and/or prism to a specific temperature. For the sake of determination of the refractive index, light is emitted by a light source at the prism sample interface at a certain angle depending on the refractive index, whereas reflected light is detected by a detector. Additionally it is mentioned, but not described in detail, that the temperature coefficient of the refractive index could be measured for films and bulk materials by measuring the index at temperatures other than room temperature, basically due to the possibility of adjusting temperature by means of the thermal elements.

All known methods for measuring the temperature coefficient of the refractive index have the disadvantage that they do not allow for measurement of temporally developing samples. Time or frequency dependent processes cannot be analyzed by the above mentioned methods. Furthermore, the above methods are unsuitable or do not describe how the temperature coefficient index could be measured in course of phase transitions of samples, or cannot be used to analyze structural formation processes.

Thus, the technical problem might be to overcome at least one of the above mentioned disadvantages or to provide an advanced method for determining the temperature coefficient of the refractive index, in particular for analyzing dynamic properties of samples.

SUMMARY OF THE INVENTION

The above technical problem is solved by the method for determination of the temperature coefficient of the refractive index of a sample wherein the refractive index of the sample is measured over a period of time and the temperature of the sample is modulated over said period of time (preferably with a known or defined temperature, and even more preferably with a known or defined temperature modulation amplitude and a known or defined temperature modulation periodicity or modulation frequency), wherein the temperature coefficient of the refractive index is calculated on the basis of the refractive index measurement over the period of time and on the basis of the temperature modulated over the period of time (or in other words, preferably on the basis of the known or defined temperature modulation over said period of time or the temperature modulation measured over said period of time, in particular on the basis of the temperature modulation amplitude and the temperature modulation periodicity or the temperature modulation frequency).

The measurement of the (complex) temperature coefficient $\phi^*(\omega)$ of the refractive index according to the method in accordance with the new invention has not been accessible before. The imaginary part of the transfer function (the temperature coefficient of the refractive index) between response (the refractive index) and the perturbation (the temperature modulation) contains information about the dynamic relaxation behavior of the sample. Due to modulation of the temperature time lags, or phase shifts respectively, may occur which provide new information with respect to the prior art methods. In general such phase shifts are related to energy losses in the sample which render new information about samples' dynamic properties. In particular, phase transitions can be observed or further characterized with the method. The method in accordance with the invention especially provides new and additional information on frequency dependent as well as on time-dependent processes. In particular, it is possible to measure the refractive index and the temperature coefficient of the refractive index under the same thermodynamic boundary conditions, preferably for the whole sample. Examples of possible investigations of time-dependent processes are polymerizations or solvent evaporations and examples of frequency-dependent processes are structural relaxations or transient phase transitions. However, the present invention is not limited to such investigations. Furthermore, the above method can be used to control and monitor processes in samples during reactions, especially for phase transitions.

In general the calculation of the temperature coefficient of the refractive index can be based either on the known/applied temperature modulation (signal) or can be based on the actual measured temperature modulation values or signal. In particular, the method in accordance with the invention may comprise measuring the temperature of the sample over the period of time and the temperature coefficient of the refractive index being calculated on the basis of the refractive index measurement over the period of time and on the basis of the measured temperature (modulation) over said period of time. This additional temperature measurement can be necessary in case of a non-optimal temperature control.

In other words the invention can also be described as a method for determining the temperature coefficient of the refractive index comprising the steps of providing a sample, measuring the refractive index of the sample over a period of time, whereas temperature of the sample is modulated over the period of time, and determining the temperature coefficient of the refractive index of the sample over the period of time, whereas the temperature coefficient of the refractive index is calculated on the basis of the refractive index measurement and the temperature modulation over the period of time.

In a preferred embodiment the amplitude of the temperature modulation is small such that a linear response of the refractive index is provided and the temperature coefficient of the refractive index follows the equation $$\phi^*(\omega) = \frac{dn^*}{dT(\omega)}$$

wherein n* is the complex refractive index, T is the temperature, and ω denotes the frequency of the temperature modulation. By restricting the amplitude of the temperature modulation to such values the calculation of the temperature coefficient can be carried out with less complexity and in particular faster, which is advantageous for a real-time calculation of the temperature coefficient of the refractive index. In addition the perturbation does not disturb or alter the process under investigation In another preferred embodiment the calculation of the temperature coefficient of the refractive index involves/comprises at least a partial Fourier transformation of the refractive index measured over the period of time and optionally of the temperature modulation over the period of time. In case of a very precise temperature modulation control, the Fourier transformation of the temperature modulation signal may be neglected. The use of Fourier transformation or fast Fourier transformation which is here understood under Fourier transformation as well, for obtaining the temperature coefficient of the refractive index constitutes an advanced method. How to carry out the calculation in detail is known to the person skilled in the art.

In another preferred embodiment the method comprises the calculation of the phase and the amplitude of each frequency component of the Fourier transform, and optionally the amplitude of each frequency component of the refractive index Fourier transform is divided by the amplitude of the respective frequency component of the temperature modulation Fourier transform, and optionally the phase of each frequency component of the temperature modulation Fourier transform is subtracted from the respective frequency component of the refractive index Fourier transform.

In another preferred embodiment the amplitude of the temperature modulation is smaller than 1 K, and preferably within the range of 0.01 K and 0.5 K. Furthermore, temperature may be modulated with a resolution of at least 0.01 K. These values allow for measurement at a quasi-static temperature and turned out to be particularly advantageous in combination with the method of the present invention.

In accordance with another preferred embodiment the temperature modulation comprises at least one of: a rectangular modulation, a sinusoidal modulation, a saw-tooth modulation, a stochastic modulation, or a multi-frequency modulation. Preferably, these types of modulations are possible, whereas the rectangular modulation or the sinusoidal modulation may facilitate and accelerate the calculation of the temperature coefficient of the refractive index. However, more complex signals could be utilized.

In accordance with yet another preferred embodiment temperature is kept essentially spatially constant over the complete sample or at least over the measured portion of the sample. In other words temperature is modulated in time but is preferably spatially constant throughout the sample. This allows having the same temperature influence on the whole sample. Thus, no (spatial) gradient is generated which might induce different reactions or processes in different regions of the sample rendering the measured data unclear or disturbing and/or influencing reactions in the sample.

In another preferred embodiment the modulation frequency ω of the temperature is in the range of $10^{-3}$ Hz to 10 Hz, and preferably between $10^{-2}$ Hz and 1 Hz. These modulation frequencies turned out to be a good compromise between measuring time and temperature inertia of the samples. Furthermore, energy losses may be pronounced for these frequencies. However, for film-like samples the frequency range could be increased up to a few kHz.

In yet another preferred embodiment the steps of the disclosed method are carried out for different frequencies of temperature modulation, such that a frequency spectroscopy of the temperature coefficient of the refractive index is obtained. Thus, by modulating or changing the modulation frequency of the temperature, it is possible to determine the frequency dependency of the temperature coefficient of the refractive index.

In another preferred embodiment the method further comprises the steps of providing a plot of the refractive index versus the time and/or modulation frequency of temperature; and/or providing a plot of the temperature coefficient of the refractive index versus the time and/or modulation frequency of the temperature. Providing such plots, especially of the temperature coefficient of the refractive index versus the time and/or the modulation frequency allows for an insight into the dynamic behavior of the temperature coefficient of the refractive index.

In another preferred embodiment the sample is subject to a phase transition during measurement (the period of time), preferably a solid-liquid transition, a glass transition, or evaporation; or is subject to a polymerization. In particular for such samples the method allows for completely new insights in the time and/or frequency dependent processes.

In accordance with yet another preferred embodiment, temperature or pressure are additionally changed within said period of time with a frequency being at least one decade, preferably two decades, lower than the modulation frequency of the temperature, such that a quasi-isothermal or quasi-isobaric measurement of the temperature coefficient of the refractive index is obtained. This measurement provides another dimension of information. If the method according to the invention is combined with a slow changing temperature of pressure as indicated above, phase transitions, e.g. between the liquid and the solid phase could be induced by such a temperature change. Similar this option could be used for, but is not limited to, evaporations, polymerizations or other phase transitions.

Preferably, the sample is isotropic or cubic symmetry and the method further comprises the step of determining the coefficient of thermal expansion by the following equation:

$$|\alpha^*(\omega)| \approx \frac{-6n_0}{(n_0^2+2)(n_0^2-1)}|\phi^*(\omega)|$$

whereas $\alpha^*(\omega)$ is the complex coefficient of the thermal expansion, $n_0$ is the equilibrium refractive index, $\phi^*(\omega)$ is the complex temperature coefficient of the refractive index determined in accordance with an embodiment of the present invention, and $\omega$ is the modulation frequency of the temperature modulation. The bars indicate absolute values as common for complex quantities. Writing the $\omega$ in round brackets indicates the frequency dependency of the preceding quantities. This formula found by the inventors turned out to offer a new and advantageous way of determining the absolute value of the coefficient of the thermal expansion in dependency of the equilibrium refractive index and the absolute value of the complex temperature coefficient of the refractive index. Although it might be known to calculate the coefficient of the thermal expansion by means of the Lorenz-Lorentz or similar relations, it has not been done with the above equation which has turned out to provide good results when compared with reference values. Furthermore, and in contrast to other known methods, the evaluation of the coefficient of thermal expansion is valid even during phase transitions between liquid and solid phases (at least in the case of non-symmetry breaking transitions or if the symmetry is limited to isotropic or cubic symmetries), whereas other methods of determination are only valid in one phase.

In another preferred embodiment the sample is measured with a refractometric system, whereas the refractometric system comprises a light source, a prism, a detector, a temperature control system, and a processing system, wherein the sample is adjoining the prism, and wherein the light source, the prism, the sample, and the detector are adapted and/or arranged to generate a beam of light, preferably with an optical frequency, passing through the prism to the sample and to detect at least a part of the beam of light reflected by the sample by the detector. In this embodiment the temperature control system is adapted to modulate at least the temperature of the sample over the period of time (preferably with a known or defined temperature, and even more preferably with a known or defined temperature modulation amplitude and a known or defined temperature modulation periodicity or modulation frequency), and the processing system is adapted to measure the refractive index over the period of time and to calculate the temperature coefficient of the refractive index on the basis of the refractive index measurement over the period of time and on the basis of the temperature modulation over the period of time (or in other words, preferably on the basis of the known or defined temperature modulation over said period of time or the temperature modulation measured over said period of time, in particular on the basis of the temperature modulation amplitude and the temperature modulation periodicity or the temperature modulation frequency). Although the use of such a refractometric system can be advantageous for allowing a calibration-less access to the dynamic properties of a sample, the method in accordance with the invention does not necessarily require the use of such a refractometric system including the mentioned components. The above mentioned device is only one of the methods for implementing the method in accordance with the invention as described in more detail below. The processing system can be integrated into a refractometer or be a separate computer being configured or adapted to carry out the above mentioned steps, optionally in real-time.

At last, the present invention is directed to a (refractometric) measurement system for determination of the temperature coefficient of the refractive index of a sample, the system comprising a light source, a detector, and optical elements, wherein the light source, the sample, the optical elements and the detector are adapted and/or arranged to measure the refractive index of the sample. Preferably, in a non-limiting example, the optical elements comprise a prism which may be arranged as usual in an Abbe refractometer. The measurement system further comprises a temperature control system adapted to modulate the temperature at least of the sample over the period of time (preferably with a known or defined temperature, and even more preferably with a known or defined temperature modulation amplitude and a known or defined temperature modulation periodicity or modulation frequency), and a processing system adapted to measure the refractive index over the period of time and adapted to determine the temperature coefficient of the refractive index on the basis of the refractive index measurement over the period of time and on the basis of the temperature modulation over the period of time (or in other words, preferably on the basis of the known or defined temperature modulation over said period of time or the temperature modulation measured over said period of time, in particular on the basis of the temperature modulation amplitude and the temperature modulation periodicity or the temperature modulation frequency). The measurement system may be an Abbe refractometer, a goniometric refractometer or an ellipsometer. The advantages of such a measurement system are basically equal to the above described advantages.

The above measurement system may additionally contain a sensor system for measuring the temperature of the sample and the processing system may be adapted to determine the temperature coefficient of the refractive index on the basis of the refractive index measurement over the period of time and on the basis of the measured temperature modulation over the period of time.

Finally it is pointed out that all above described embodiments may be combined with each other.

BRIEF DESCRIPTION OF DRAWINGS

In the following the figures showing at least one non-limiting embodiment in accordance with the invention are briefly described. More details and alternatives are described in the detailed description of the embodiments.

DETAILED DESCRIPTION OF THE EMBODIMENTS

Figure 1:
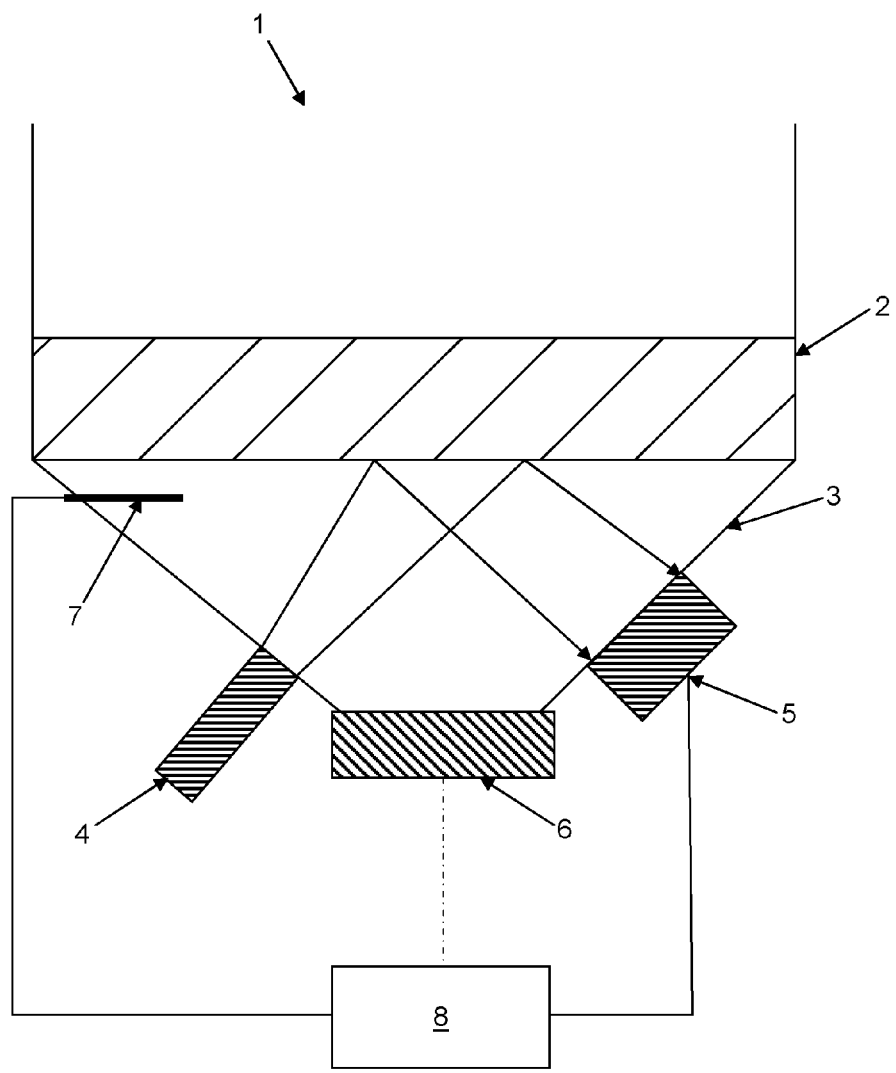
FIG. 1 shows a scheme of an exemplary refractometer for carrying out the method in accordance with an embodiment of the invention.

FIG. 1 depicts a scheme of a refractometer 1. A sample 2 is adjoining a prism 3 either in direct contact with each other or in indirect contact via a suitable immersion liquid. Furthermore, the setup of FIG. 1 includes a light source 4 generating a light beam positioned at a first side of the prism 1. The light source 4 is further arranged such that light is guided through the prism 3 onto the sample 2 at the interface between sample 2 and the prism 3, i.e. a second side of the prism 3. At least a part of the light beam is reflected through the prism 3 back to a light detector 5 which is arranged at a third side of the prism 3. Preferably, the light beam has optical wavelengths though other frequencies may be used as well. The refractometer 1 further comprises a temperature control system 6, preferably adapted to control the temperature of the sample 2 and preferably of the prism 3. The temperature control system 6 may further comprise a temperature sensor system 7 allowing for a feedback of the actual temperature of the sample 2 and/or the prism 3. Thus, it is possible to measure the actual temperature (signal) of the sample 2 and thus to use this, if desired, for the calculation of the temperature coefficient of the refractive index as described in more detail below. The temperature control system 6 is adapted to generate a modulated temperature, preferably spatially constant throughout the complete sample 2. The temperature control system 6 is preferably adapted to generate a sinus signal, a saw tooth signal, or other types of multi-frequency signals, or even stochastic signals. In particular, the temperature control system 6 comprises also a cooler and/or heater system (not shown in detail). Such a system may comprise for example a Peltier heater/cooler. Furthermore, the system as depicted in FIG. 1 comprises a processing system 8. The processing system 8 is adapted to receive data or signals from the light detector 5 and optionally from the temperature control system 6 and/or from the temperature sensor system 7. In particular, the processing system 8 is adapted to calculate the temperature coefficient of the refractive index based on the refractive index measurement (signal) and either on the (known) temperature modulation or alternatively based on the measured (actual) temperature modulation signal or values which may be measured by the temperature sensor system 7. The optical assembly as such, i.e. the prism 3, the light source 4, the light detector 5 and their arrangement for measuring the sample 2, is in general known as an Abbe refractometer. The light source 4 can be e.g. a laser or a LED, the prism 3 can be an Yttrium aluminum garnet (YAG) or another suitable material.

In general sample 2 can be a liquid or solid. Polymers may be of special interest. Preferably, the sample 2 is transparent. The size of the sample 2 can be chosen by the person skilled in the art depending on the specific design of the utilized measurement device. However, the method in accordance with the invention is not limited to such samples. In general, all samples for which the refractive index can be determined are suitable for the method in accordance with the present invention.

Moreover, it is pointed out that it is known in the state of the art how to measure (determine) the refractive index by multiple methods, as for example goniometry, ellipsometry, or Abbe refractometry. The applicant points out that not only Abbe refractometry can be used to carry out the invention. The skilled person could also implement a similar temperature modulation for a goniometer (goniometric refractometer) in which the sample 2 itself has a prism-like shape. Alternatively, the sample 2 is prepared in form of a film or flat sample as used in ellipsometry. Thus, the invention shall not be limited to the use of the above described refractometer 1.

However, Abbe refractometry offers some advantages as for example high measurement accuracy and negligible geometric changes of the sample 2, wherein the latter results from the fact that the measurement is directed essentially to the boundary region of the sample 2 in contact with the prism 3. Another advantage of Abbe refractometry is that no calibration is needed for each measured sample.

Even in case of using Abbe refractometry, the above design of a refractometer 1 for carrying out the method in accordance with the present invention can include different light sources, prisms, or detectors or can feature another arrangement or path of light as known by the person skilled in the art.

In general, the refractive index is measured in the prior art for essentially one point in time. In contrast, according to the present invention the refractive index is measured over a period of time wherein temperature is modulated within this period. By knowing the signal of the temperature modulation and the measured refractive index (values/signal) over the period of time, it is possible to determine the coefficient of the refractive index over the period of time.

In particular, Fourier transformation can be used to calculate the temperature coefficient of the refractive index. However, this is only one method to calculate the temperature coefficient. Of course, the method of Fourier transformation as such is known to the skilled person. The extent of the transformation depends basically on the complexity of the temperature modulation and/or on the desired accuracy.

In general the refractive index n is a complex value n*. Because of structural relaxation phenomena, perturbations, as e.g. temperature modulation, can result in a phase shift, i.e. a time lag in the response of the sample. The connecting quantity between the temperature perturbation or modulation and the response of the refractive index is the temperature coefficient of the refractive index which is in general also a complex quantity. In general, the imaginary part of the transfer function between response and perturbation contains information about the dynamic relaxational behavior and can contain information about structural relaxations. Although being not necessary, for an easier interpretation in terms of proportionality, the perturbation can be small such that linear response conditions can be assumed with negligible errors. If the amplitude of temperature modulation is small enough, a simple description of the temperature coefficient of the refractive index $\phi^*(\omega)$ (in general a complex parameter) can be described by the relation $$\phi^* = \frac{dn^*}{dT},$$

wherein n* denotes the complex refractive index and T denotes the temperature. In the experiments of the applicant temperature amplitudes of less than 1 K have turned out to be preferable. The resolution of the temperature modulation should be of less than 0.01 K. Using the assumption or prerequisite of a linear response may thus substantially simplify the extent of calculation.

If for example the temperature modulation or perturbation is a rather simple mono-frequency sinusoidal perturbation and if a linear response is assumed, the calculation can be very easy and may preferably comprise the following steps.

First, the refractive index is measured over a period of time, wherein the period of time corresponds to at least one period P of the sinus signal or function. Preferably, the measured signal (SIG) can be averaged over one period P to obtain the average value $SIG_{DC}$. This value can be subtracted from the measured signal SIG, so that only the oscillation centered around zero, i.e. $SIG_{AC}=SIG-SIG_{DC}$, remains. In a next step the signal $SIG_{AC}$ can be multiplied with $$\sin\left(2\pi \frac{t}{p}\right) \text{ and } \cos\left(2\pi \frac{t}{p}\right)$$

resulting in $SIG_{SIN}$ and $SIG_{COS}$. Afterwards each function $SIG_{SIN}$ and $SIG_{COS}$ can be averaged over one period P to obtain the constant values $SIG_{SIN\_DC}$ and $SIG_{COS\_DC}$. The amplitude A of the signal can then be calculated via the generally known relation $A=2\cdot\sqrt{SIG_{SIN\_DC}^2+SIG_{COS\_DC}^2}$ and the phase $\phi$ via the well known relation $$\varphi = \arctan\left(\frac{SIG_{SIN\_DC}}{SIG_{COS\_DC}}\right).$$

This operation is preferably applied to the refractive index measurement, and optionally also to the measured modulated temperature (signal). This is especially of advantage if the temperature control is not expected to be accurate. The temperature coefficient of the refractive index may then be calculated by dividing the amplitude of the refractive index by the amplitude of the temperature modulation. The phase of the temperature coefficient of the refractive index can then be obtained by subtracting the phase of the temperature perturbation from the phase of the refractive index signal.

Thus, the above described method for calculating the temperature coefficient of the refractive index constitutes a short lock-in algorithm or in other words, involves a short Fourier transformation. This calculation can preferably be performed in real-time. The calculation of amplitude and phase of the refractive index and preferably of the temperature modulation signal or function is known by the person skilled in the art in general.

The above example of calculating the temperature coefficient of the refractive index in case of a sinusoidal signal constitutes merely a non-limiting example of the invention.

For more complex, i.e. non-sinusoidal, modulations, as e.g. multi-frequency perturbations a (full) Fourier transformation can be applied to the refractive index signal and optionally also to the temperature signal. In this case, amplitude and phase have to be evaluated (as described above) for each frequency component of the respective Fourier transform. How to carry out the calculation in detail, depends on the concrete case and can be carried out by the person skilled in the art depending on the specific case.

The periods of temperature modulation may preferably be in the order of 1 s to 300 s corresponding essentially to frequencies of ca. $10^{-3}$ Hz to 1 Hz. Higher frequencies are not favorable because of thermal inertia. The period of time for measuring the refractive index and for determining the temperature coefficient of the refractive index are preferably at least as long as one modulation period of the temperature which may be described by $P=2\pi/\omega=1/f$, whereas P is the temperature modulation period and f is the frequency of the modulation. The period of time for measuring the refractive index may comprise multiple modulation periods as for example for observing or monitoring a chemical and/or physical reaction in a sample over a period of time, as e.g. phase transitions, polymerizations, solvent evaporations, etc.

Additionally, the temperature can be changed with a frequency which is at least one decade, preferably two decades, lower than the used temperature modulation frequency $\omega$. Thus, it is possible to measure the temperature coefficient at quasi-static temperatures with the above described method but with additional information about a temperature dependency in general. The same applies to a change in pressure allowing for quasi-isobaric measurements of the temperature coefficient of the refractive index. In particular, temperature or pressure could be changed for example linearly or by means of another function provided that the change is slow in comparison with the frequency of the temperature modulation as for instance preferably only in the order of the amplitude of the temperature modulation over one period.

Furthermore, it is possible to vary or modulate the frequency of the temperature modulation obtaining a kind of refractometric spectroscopy. In particular measurements could be made for multiple (discrete) modulation frequencies $\omega$.

The method in accordance with the invention allows thus for investigation of time dependent processes of liquid, solid and especially of polymer samples.

Figure 2:
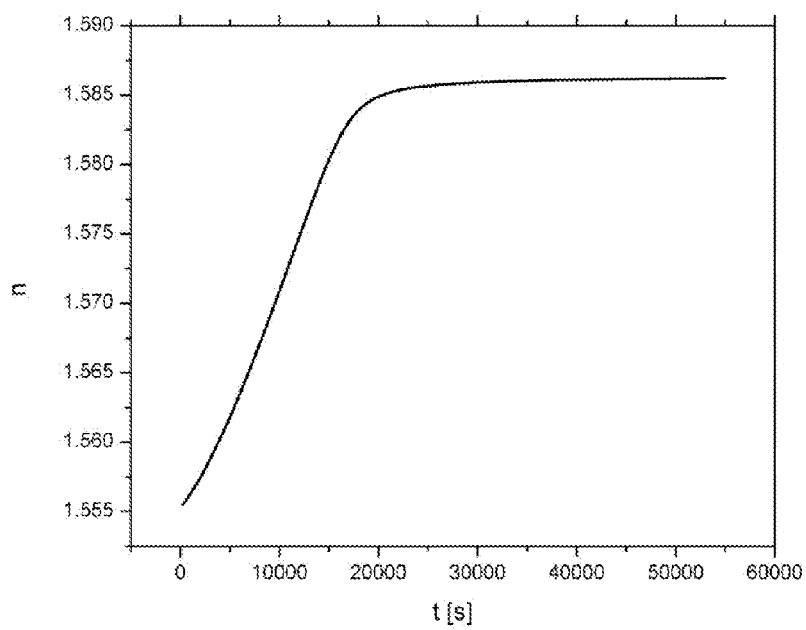
FIG. 2 shows a graph of a time dependent refractive index measurement obtained with a method in accordance with the invention.
Figure 3:
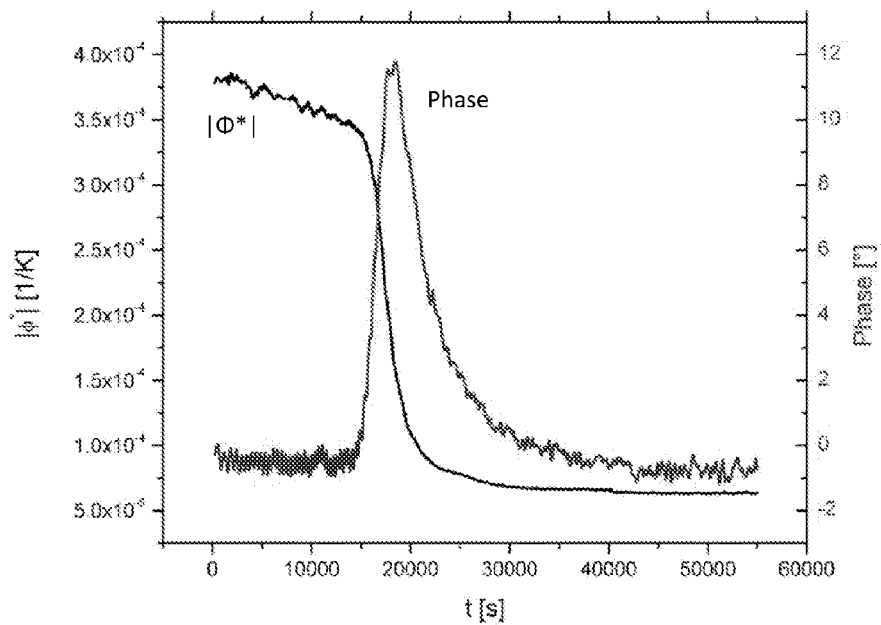
FIG. 3 shows a graph of the modulus of the time dependent temperature coefficient of the refractive index obtained with the method in accordance with the present invention under the same thermodynamic boundary conditions as with respect to FIG. 2.

In the following, the advantages of the method shall be described in view of a non-limiting example of a glass transition of a polymer sample. In this example a glass transition is chemically induced in an epoxy material, whereas the sample is driven isothermally into the glassy state by polymerization which is a non-equilibrium process. The temperature perturbation or modulation according to the invention allows for an quasi-isothermal measurement of the frequency depending property $\phi^*(t, \omega)$ and the (quasi-)static refractive index n(t) as a function of time t at a given temperature T. The modulation frequency for this example is about $107=8$ mHz. Alternatively, the glass transition could also be thermally induced by change in the average temperature resulting in a quasi-static measurement as a function of temperature instead of time. The temperature modulation in accordance with the invention allows for parallel measurement of the dynamic properties of the sample in terms of $\phi^*(T(t), \omega)$ and the (quasi-)static property in terms of n(T(t)) under the same thermodynamic boundary conditions. FIGS. 2 and 3 depict the results of a measurement in accordance with the invention. FIG. 2 shows the measured refractive index n in dependency of the time t. Apparently only a smooth monotonous evolution is observed but no anomaly that could be assigned to the glass transition. The corresponding temporal evolution of the temperature coefficient of the refractive index $\phi^*(t,\omega)$ is shown in FIG. 3. Here the chemically induced glass transition is well visible by the step like decrease in the modulus of $\phi^*(t,\omega)$ and the related appearance of a non-zero phase lag due to chemically induced structural relaxations. Hence, the mere measurement of the refractive index could not lead to the identification of the glass transition for this sample but the new method of additionally determining the frequency dependent temperature coefficient of the refractive index based on temperature modulation and refractive index measurement allows for investigation of a temporally driven process in the sample like the chemically induced glass transition visible in FIG. 3.

Thus, a new method for analyzing time dependent and/or frequency dependent processes in samples is obtained. The combination of the measurement of a quasi static property (i.e. the refractive index) and the dynamic property (i.e. the temperature coefficient of the refractive index determined with a modulated temperature) yields new information about structure formation processes. The method could also be used to control processes in real-time. In particular, a structure formation could be observed by the present method in real-time and be influenced in a desired point in time.

In a preferred embodiment of the invention the coefficient of the thermal expansion can additionally be calculated based on the retrieved temperature coefficient of the refractive index by means of a verified relation between both. It is assumed (and known) that the change in the refractive index basically results from the change of mass density and that the response of the sample to the perturbation is linear. In other words, there should exist a relation between the temperature coefficient s of the refractive index and the coefficient of thermal expansion. The measurements of $\phi^*(\omega)$ in accordance with the present invention allows now for deduction of the coefficient of thermal expansion (CTE) $\alpha^*(\omega)$, such that $$|\alpha^*(\omega)| = \frac{-6n_0}{(n_0^2 + 2)(n_0^2 - 1)}|\Phi^*(\omega)|$$

which has been deduced by the inventors can be used to calculate the modulus of the CTE. Consequently, a new method for obtaining the coefficient of thermal expansion based on measurement of the frequency dependent temperature coefficient of the refractive index is provided. Although there are other known techniques to obtain the CTE as for example thermal mechanical analysis or pyknometry and vibrational densimetry, the CTE cannot be measured by the known methods across transitions from the solid to the liquid phase because the above techniques are only suitable for one of the phases. Especially for optical frequencies this additional calculation step has turned out to issue well results.

Finally it is remarked that all above described features can be adapted or combined with each other by a person skilled in the art for a specific implementation of the invention depending on the circumstances.

The invention claimed is:

1. A method for determination of a temperature coefficient of a refractive index of a sample, wherein the determination of the temperature coefficient of the refractive index of the sample is based on a refractive index measurement, said method comprising:
   measuring a refractive index of the sample over a period of time, wherein a defined temperature of the sample is modulated over the period of time;
   measuring the modulation of the temperature over the period of time; and
   calculating a temperature coefficient of the refractive index based on the sample's refractive index measurement over the period of time and on the measured temperature modulation over the period of time.

2. The method in accordance with claim 1, wherein an amplitude of the temperature modulation is small such that a linear response of the refractive index is provided and the temperature coefficient of the refractive index can be described by the equation $$\Phi^*(\omega) = \frac{dn^*}{dT(\omega)},$$

wherein $n^*$ is the complex refractive index, T is the temperature, and $\omega$ denotes the frequency of the temperature modulation.

3. The method in accordance with claim 2, wherein the calculation of the temperature coefficient of the refractive index comprises using at least a partial Fourier transformation of the refractive index measured over the period of time and of the temperature modulation over the period of time.

4. The method in accordance with claim 3, further comprising calculating the phase and the amplitude of each frequency component of the Fourier transform.

5. The method in accordance with claim 3, wherein at least one of:
   the amplitude of each frequency component of the refractive index Fourier transform is divided by the amplitude of the respective frequency component of the temperature modulation Fourier transform, and
   the phase of each frequency component of the temperature modulation Fourier transform is subtracted from the respective frequency component of the refractive index Fourier transform.

6. The method in accordance with claim 1, wherein at least one of:
   an amplitude of the temperature modulation is smaller than 1 K,
   the amplitude of the temperature modulation is within the range of 0.01 K and 0.5K, and
   the temperature is modulated with a resolution of at least 0.01 K.

7. The method in accordance with claim 6 wherein the temperature modulation comprises at least one of: a rectangular modulation, a sinusoidal modulation, a saw-tooth modulation, a stochastic modulation, or a multi-frequency modulation.

8. The method in accordance with claim 7, wherein the temperature is kept essentially, spatially constant over the complete sample.

9. The method in accordance with claim 8, wherein at least one of:
   the modulation frequency of the temperature is in the range of $10^{-3}$ Hz to 10 Hz, and
   the modulation frequency of the temperature is between $10^{-2}$ Hz and 1 Hz.

10. The method in accordance with claim 9, wherein the measuring of the refractive index of the sample over a period of time is carried out for different frequencies of temperature modulation, such that a frequency spectroscopy of the temperature coefficient of the refractive index is obtained.

11. The method in accordance with claim 10, whereas the sample is subject to at least one of:
   a solid-liquid transition phase transition during measurement,
   a glass transition during measurement,
   an evaporation during measurement, and
   a polymerization.

12. The method in accordance with claim 11, further comprising changing at least one of the temperature and a pressure within the period of time with a frequency being at least one of at least one decade lower than the modulation frequency of the temperature, and at least two decades lower than the modulation frequency of the temperature, such that one of a quasi-isothermal and a quasi-isobaric measurement of the temperature coefficient of the refractive index is obtained.

13. The method in accordance with claim 12, wherein the method further comprises determining a coefficient of thermal expansion utilizing the equation $$|\alpha^*(\omega)| = \frac{-6n_0}{(n_0^2 + 2)(n_0^2 - 1)}|\Phi^*(\omega)|,$$

wherein $\alpha^*(\omega)$ is the complex coefficient of the thermal expansion; $n_0$ is the equilibrium refractive index; and $\Phi^*(\omega)$ is the complex temperature coefficient of the refractive index; and $\omega$ is the modulation frequency of the temperature modulation.

14. The method in accordance with claim 13, wherein the refractive index of the sample is measured over the period of time utilizing a refractometer system comprising:
   a light source,
   a prism,
   a detector,
   a temperature control system, and
   a processing system,
   wherein the sample is adjoining the prism, and wherein
   the light source, the prism, the sample, and the detector are structured and operable to generate a beam of light, with an optical wavelength, passing through the prism to the sample, and to detect at least a part of the beam of light reflected by the sample by the detector, and wherein
   the temperature control system is operable to modulate at least the temperature of the sample over the period of time, and
   the processing system is operable to measure the refractive index over the period of time and calculate the temperature coefficient of the refractive index on the basis of the refractive index measurement over the period of time and on the basis of the temperature modulation over the period of time.

15. A measurement system for determination of the temperature coefficient of the refractive index of a sample, said system comprising:
   a light source, a detector system, and optical elements, wherein the light source, the sample, the optical elements and the detector system are structured and operable to measure the refractive index of the sample;
   a temperature control system structured and operable to modulate a defined temperature at least of the sample over the period of time;
   a temperature sensor system for measuring the modulation of the temperature; and
   a processing system structured and operable to determine the temperature coefficient of the refractive index based on the refractive index measurement over the period of time and on the temperature modulation as measured by the temperature sensor system over the period of time.

* * * * *